United States Patent [19]

Otsuka et al.

[11] 4,420,470

[45] Dec. 13, 1983

[54] PERCUTANEOUS ABSORPTION TYPE PHARMACEUTICAL PREPARATION OF ISOSORBIDE DINITRATE OR PENTAERYTHRITOL TETRANITRATE IN PRESSURE-SENSITIVE LAMINATE

[75] Inventors: Saburo Otsuka; Toshiyuki Yoshikawa; Shoichi Tokuda; Yuuseke Ito, all of Ibaraki, Japan

[73] Assignees: Nitto Electric Industrial Co., Ltd., Osaka; Toa Eiyo Ltd., Tokyo, both of Japan

[21] Appl. No.: 338,190

[22] Filed: Jan. 8, 1982

[30] Foreign Application Priority Data

Jan. 8, 1981 [JP] Japan .................................. 56-1805

[51] Int. Cl.$^3$ ...................... A61L 15/03; A61F 13/00; A61K 9/70
[52] U.S. Cl. ...................................................... 424/28
[58] Field of Search ........................................ 424/28

[56] References Cited

U.S. PATENT DOCUMENTS

| | | | |
|---|---|---|---|
| 3,742,951 | 7/1973 | Zaffaroni | 424/28 |
| 3,972,995 | 8/1976 | Tsuk et al. | 424/28 |
| 4,291,015 | 9/1981 | Keith et al. | 424/28 |
| 4,336,243 | 6/1982 | Sanvordeker | 424/28 |

FOREIGN PATENT DOCUMENTS

| | | | |
|---|---|---|---|
| 45-12314 | 5/1970 | Japan | 424/28 |
| 52-18813 | 2/1977 | Japan | 424/28 |
| 55-122714 | 9/1980 | Japan | 424/28 |
| 2021610A | 12/1979 | United Kingdom | 424/80 |
| 2021950A | 12/1979 | United Kingdom | 424/28 |
| 2073588A | 10/1981 | United Kingdom | 424/28 |

OTHER PUBLICATIONS

Dasta et al., "Topical Nitroglycerin", pp. 29–35 American Pharmacy N322(2), Feb. 1982.
Nitto Electric Ind. K.K., (Jul. 1980) Japan 55-92314, Derwent 61118 C/35, Abstract Card.
Toyo Ink Mfg. K.K. (Feb. 1980), Japan 55-20726, Derwent 22580 C/13, Abstract Card.
Uchimura K., (Feb. 1977), Japan 52-18812, Derwent 21065Y/12, Abstract Card.

*Primary Examiner*—Shep K. Rose
*Attorney, Agent, or Firm*—Sughrue, Mion, Zinn, Macpeak & Seas

[57] ABSTRACT

A pharmaceutical preparation comprising a flexible backing and a base material provided thereon is described wherein the base material consists essentially of a polymer having a glass transition temperature of from $-70°$ C. to $-10°$ C. and exhibiting pressure-sensitivity at room temperature, and isosorbide dinitrate or pentaerythritol tetranitrate. This pharmaceutical preparation is applied to the skin, and permits the active ingredient to be absorbed through the skin into the body at a constant rate, and gradually over a long period of time.

11 Claims, No Drawings

PERCUTANEOUS ABSORPTION TYPE PHARMACEUTICAL PREPARATION OF ISOSORBIDE DINITRATE OR PENTAERYTHRITOL TETRANITRATE IN PRESSURE-SENSITIVE LAMINATE

FIELD OF THE INVENTION

The present invention relates to a pharmaceutical preparation that is applied to the skin so that active ingredients are absorbed therethrough into the body (hereinafter the pharmaceutical preparation is referred to as "percutaneous absorption type pharmaceutical preparation"). More particularly, it is concerned with a percutaneous absorption type pharmaceutical preparation comprising a base material containing isosorbide dinitrate (ISDN) or pentaerythritol tetranitrate (PETN) which is effective to suppress or prevent attacks of angina pectoris.

BACKGROUND OF THE INVENTION

Nitroglycerin is known as a medicine for angina pectoris (i.e., a coronary vasodilator) and is used in an ointment form which can be sealed and stored.

Recently, a pharmaceutical preparation in a tape form has been proposed, which comprises a backing and a pressure-sensitive adhesive layer with nitroglycerin incorporated thereinto on the backing. This type of pharmaceutical preparation, however, has not yet been put into practical use, since it cannot be stored due to the high volatility of the nitroglycerin, and the excessive percutaneous absorbability of nitroglycerin causes harmful side effects such as skin irritator.

Isosorbide dinitrate (ISDN) and pentaerythritol tetranitrate (PETN) are known to be effective in the suppression or prevention of attacks of angina pectoris, and they are generally used in a tablet form. From a viewpoint of suppression or prevention, it is desirable that they are supplied into the body at a constant rate, and gradually over a long period of time.

Various attempts, therefore, have been made to control the solubility characteristics of the tablet. However, since the absorbability of medicine varies depending on the pH in the stomach or intestines, the presence of contents, etc., it is generally impossible to supply the ISDN or PETN at a constant rate and gradually over a long period of time.

SUMMARY OF THE INVENTION

The principal object of the invention is to provide a percutaneous absorption type pharmaceutical preparation which permits supplying ISDN or PETN at a constant rate and gradually over a long period of time.

It has now been found that this object can be attained by providing a base material comprising a polymer whose glass transition temperature (Tg) is adjusted to −70° C. to −10° C. and which is pressure-sensitive at room temperature and ISDN or PETN, coated on a flexible backing.

The present invention, therefore, relates to a pharmaceutical preparation comprising a flexible backing and a base material provided on the backing, said base material comprising a polymer having a glass transition temperature (Tg) of from −70° C. to −10° C. and exhibiting pressure-sensitivity at room temperature, and isosorbide dinitrate (ISDN) or pentaerythritol tetranitrate (PETN).

DETAILED DESCRIPTION OF THE INVENTION

Polymers having a glass transition temperature (Tg) (measured using a differential scanning colorimeter) of less than −70° C. are not suitable for use in the invention in that they reduce the shape retention properties of the base material and leave residues on the skin, and furthermore, in peeling the pharmaceutical preparation, they provide physical irritation to the skin. Also, polymers having a glass transition temperature (Tg) of more than −10° C. are not suitable for use in the invention since they reduce the mobility of active ingredients in the polymeric substance, reducing the releasability thereof, and furthermore, reduce the adhesion of the pharmaceutical preparation to the skin. Moreover, when the glass transition temperature (Tg) is more than −10° C., the dissolution and dispersion of the active ingredients in the polymer in the production of the base material become insufficient, and in some cases, a major portion of the active ingredient does not contribute to the treatment.

The optimum glass transition temperature (Tg) is from −55° C. to −25° C. Polymers having a Tg of −70° C. to −10° C. and exhibiting pressure-sensitivity at room temperature can be selected, e.g., from synthetic resins and rubbers as set forth below:

Synthetic resins include polyvinyl alkyl ethers, polyacrylates, polymethacrylates, polyurethanes, polyesters, polyamides, and ethylene-vinyl acetate copolymers. Rubbers include styrene-isoprene-styrene block copolymer rubber, styrene-butadiene rubber, polybutene rubber, polyisoprene rubber, butyl rubber, silicone rubber, and natural rubber.

When these synthetic resins or rubbers per se do not have a glass transition temperature falling within the above-described range, they can be used in combination with other polymers, or alternatively, additives which are generally known can be added to adjust the glass transition temperature falling within the desired range.

It has been found that acryl-based copolymers can meet the above-described requirements of adhesiveness, compatibility, solubility and releasability most surely and by a relatively simple procedure in the system in combination with ISDN or PETN. Preferred acryl-based copolymers contain at least 50% by weight of alkyl acrylate or alkyl methacrylate containing an average of at least 4 carbon atoms in the alkyl moiety.

These acryl-based copolymers exhibit good adhesiveness to the skin and good solubility to active ingredients, and furthermore, less irritate the skin, and hold the active ingredients stably.

The acryl-based copolymers as used herein include copolymers of alkyl acrylate or methacrylate and other copolymerizable functional monomers. These monomers are compounded in an amount of up to 20% by weight and preferably 0.5 to 15% by weight. By varying the amount of the monomer added, the cohesive properties of the resulting acryl-based copolymer can be changed, and therefore, the release rate or release amount of the active ingredient from the base material can be controlled. Also, it is possible to increase the hydrophilic properties of the acryl-based copolymer by selecting the type of the monomer.

In addition, the acryl-based copolymers as used herein include copolymers of alkyl acrylate or methacrylate and other copolymerizable vinyl ester monomers. These monomers are compounded in an amount of up to 40% by weight, and preferably from 10 to 30% by weight. Acryl-based copolymers containing such vinyl ester monomers have a high solubility to the active ingredients.

Thus, it can be understood that acryl-based copolymers composed of at least 50% by weight of alkyl acrylate or methacrylate, from 0 to 20% by weight of functional monomer copolymerizable with the alkyl acrylate or methacrylate, and from 0 to 40% by weight of vinyl ester monomer copolymerizable with the alkyl acrylate or methacrylate are suitable to support therein ISDN or PETN.

Alkyl acrylates and alkyl methacrylates which can be used include n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers copolymerizable with the above alkyl acrylates or methacrylates which can be used include acrylic acid, methacrylic acid, itaconic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, ethoxyethyl acrylate and ethoxyethyl methacrylate.

Vinyl ester monomers copolymerizable with the above alkyl acrylates or methacrylates which can be used include vinyl acetate and vinyl propionate.

The amount of the active ingredients added is generally from about 0.5 to 20% by weight, and preferably from about 2 to 15% by weight, based on the total weight of the polymer (or copolymer) and the active ingredients, i.e., the weight of the base material, The thus-prepared base material is coated on a flexible backing, usually in a thickness of from 5 to 300 μm. The base material can be coated on the backing entirely or partially, for example, in a striped, checked, wave, or other form as well as uniformly.

In a preferred further embodiment of the pharmaceutical preparation of the invention, each base material containing two or more polymers having different glass transition temperature is coated on the backing one by one on one side thereof in a predetermined width, or is coated alternatively in a predetermined width, or is coated in an insular form. This modified pharmaceutical preparation has the advantage that since the polymers constituting the base material have different active ingredient-release rates due to the differences in the glass transition temperature, the total active ingredient-release period of the pharmaceutical preparation can be lengthened compared with pharmaceutical preparation having a base material in which a polymer having a single glass transition temperature is used. The effects obtained by coating the base material in such patterns can also be obtained by changing the coating thickness of the base material and/or the concentration of the active ingredient.

Another preferred embodiment of the pharmaceutical preparation of the invention is to superpose a plurality of base material layers on the backing. In this modified pharmaceutical preparation, the concentration of the active ingredient in the base material layer is arranged so that it increases toward the backing, i.e., the concentration of the active ingredient in the lowermost layer is highest, and that in the uppermost layer is lowest, so that the active ingredient is supplied successively from lower layers to upper layers. This type of pharmaceutical preparation has the effect of preventing the percutaneous absorption of a large amount of active ingredient immediately after the application of the pharmaceutical preparation onto the skin. Thus, it can be understood that a pharmaceutical preparation having the same lamination structure as above with the exception that the gradient of concentration is reversed can be used as a pharmaceutical preparation producing an immediate effect, i.e., permitting the percutaneous absorption of the active ingredient in a short period of time.

Any backing can be used in the invention so long as it has flexibility to the extent that when applied onto the skin, it does not produce a significant unpleasant feeling.

Suitable examples of flexible backings which can be used include films or sheets of polyolefin, polyester, polyurethane, polyvinyl alcohol, polyvinylidene chloride, polyamide, ethylene-vinylacetate copolymer (EVA), ethylene-ethylacrylate copolymer (EEA), etc., metal-vapor deposited films or sheets thereof, rubber sheets or films, expanded synthetic resin sheets or films, unwoven fabrics, fabrics, knitted fabrics, paper, and foils. Those backings can be used individually or in the laminates thereof. Particularly, the use of a laminate having a copolymer such as EVA or EEA, e.g., a laminate of a polyester and EVA or a laminate of a polyester and EEA, provides the following advantage. When the base material is formed on the laminate (backing) such that the base material contacts the polymer of the laminate, if ISDN or PETN is blended in the base material in an amount more than the saturated solubility of the polymer, the copolymer layer adsorbs ISDN or PETN and crystallized product of the ISDN or PETN is not formed on the surface of base material, which does not result in lowering the adhesion of the pharmaceutical preparation to the skin.

When backings having substantially no air permeability or moisture permeability are used, it is preferred to provide holes, slits, etc., by physical or chemical techniques since ISDN or PETN sometimes causes itching, etc., on the skin depending on the concentration thereof.

In order to prevent the peeling-off of the pharmaceutical preparation and to reduce any unpleasant feeling, it is preferred to use backings which can stretch at least 10%, or which had been subjected to a stretch-contraction treatment.

In a base material as described herein, there can also be incorporated fillers and absorption promotors, in order to better achieve the objects of keeping the shape retention properties of the base material, increasing the absorbability of the active ingredient through the skin into the body, and so forth. In addition, the base material may contain small amounts of additives such as a tackifier, a softening agent, and other chemicals such as an itching-preventing agent.

Fillers which can be used include silica fine powder, titanium white, and calcium carbonate. Absorption promotors which can be used include alcohols such as propylene glycol, and diethylene glycol, salicylic acid, urea, allantoin, dimethyl sulfoxide, dimethylacetamide, dimethylformamide, diisopropyl adipate, diethyl sebacate, ethyl laurate, methyl nicotinate and nicotinic acid.

The amount of the filler added is 20% by weight or less based on the weight of the base material, and the amount of the absorption promotor added is 30% by weight or less based on the weight of the base material.

The important feature of the pharmaceutical preparation of the invention that ISDN or PETN is supplied and absorbed at a constant rate and gradually over a long period of time will become apparent from the examples as set forth below. All parts are by weight.

EXAMPLE 1

|  | parts |
| --- | --- |
| Polyisoprene rubber | 45 |
| Liquid paraffin | 15 |
| Lanolin | 5 |
| Aliphatic petroleum resin | 35 |

This composition (Tg: −35° C.) was melted at 120° C. for 4 hours in inert gas, and cooled to 73° C. Then, 2 parts of ISDN was added thereto, and the mixture was thoroughly stirred to prepare a base material. The base material thus-prepared was flow-coated in a thickness of 100 μm onto one surface of a foamed polyethylene sheet to obtain a pharmaceutical preparation.

EXAMPLE 2

|  | parts |
| --- | --- |
| Polyisobutylene rubber (viscosity-average molecular weight: 1,200,000) | 20 |
| Polyisobutylene rubber (viscosity-average molecular weight: 35,000) | 30 |
| Polybutene | 20 |
| Wood rosin | 30 |
| Toluene/ethyl acetate (2/1 by weight) | 250 |

This composition (Tg: −40° C.) was mixed by the method as described hereinafter to prepare a base material solution. The base material solution thus-prepared was coated on a releasing liner and dried to provide a coating film having a dry thickness of 100 μm. The coating film then adhered to a soft polyvinyl chloride film to obtain a pharmaceutical preparation.

Mixing Method

Seven parts of PETN was dissolved in a mixed solvent of toluene and ethyl acetate, and polyisobutylene rubber was thoroughly dissolved therein. Then, the polybutene and wood rosin were added, and the resulting mixture was thoroughly stirred to prepare the base material solution.

EXAMPLE 3

A mixture of 50 parts of isooctyl acrylate and 50 parts of butyl acrylate was placed in a three-necked flask, and 25 parts of ethyl acetate was added thereto in an atmosphere of inert gas. They were polymerized at a temperature of 60° to 64° C. for 8 hours by the use of 0.3 part of azobisisobutyronitrile as a polymerization initiator while adding dropwise ethyl acetate to obtain a solution of a copolymer (Tg: −51° C.), having a solids content of 40% by weight and a viscosity of 410 poises (at 30° C.).

To 100 parts (as solids) of the solution was added 8 parts of ISDN, and the resulting mixture was stirred and coated on a releasing liner in a dry thickness of 50 μm to form a coating film. The coating film thus-prepared then adhered to a polyethylene film to obtain a pharmaceutical preparation.

EXAMPLE 4

|  | parts |
| --- | --- |
| 2-Ethylhexyl acrylate | 93 |
| Acrylic acid | 7 |

Using this composition, a pharmaceutical preparation was prepared by the same method as in Example 3 except that the backing was a laminate of 4 μm thick polyester and 5 μm thick EVA.

The thus-prepared copolymer (Tg: −55° C.) solution had a solids content of 40% by weight and a viscosity of 805 poises.

EXAMPLE 5

|  | parts |
| --- | --- |
| 2-Ethylhexyl acrylate | 74 |
| Acrylic acid | 6 |
| Vinyl acetate | 20 |

Using this composition, a pharmaceutical preparation was prepared by the same method as in Example 3.

The thus-prepared copolymer (Tg: −45° C.) solution had a solids content of 37% by weight and a viscosity of 530 poises.

EXAMPLE 6

|  | parts |
| --- | --- |
| 2-Ethylhexyl acrylate | 55 |
| Ethoxyethyl acrylate | 15 |
| Vinyl acetate | 30 |

Using this composition, a pharmaceutical preparation was prepared by the same method as in Example 3.

The thus-prepared copolymer (Tg: −47° C.) solution had a solids content of 63% by weight and a viscosity of 690 poises. In this example, as a backing, a polyester film was used.

EXAMPLE 7

The base material solutions prepared in Examples 4 and 5 were each coated on one side of a polyester film in a width of 40 mm and dried to prepare a pharmaceutical preparation having two base material layers, each having a thickness of 50 μm.

The pharmaceutical preparations prepared in Examples 1 to 7 were tested, and the results are shown in Tables 1 and 2.

TABLE 1

| Example No. | Adhesion to Skin | | Residual Content of Active Ingredient (%) | Mobility of Active Ingredient to Skin (hours) | | | | | | | | | |
| --- | --- | --- | --- | --- | --- | --- | --- | --- | --- | --- | --- | --- | --- |
| | Initial | After 8 Hours | | 1/6 | 2/6 | 3/6 | 4/6 | 1 | 3 | 8 | 12 | 24 | 48 |
| 1 | Good | Fair | 89 | — | — | — | — | o | o | o | o | o | o |

TABLE 1-continued

| Example No. | Adhesion to Skin Initial | Adhesion to Skin After 8 Hours | Residual Content of Active Ingredient (%) | Mobility of Active Ingredient to Skin (hours) 1/6 | 2/6 | 3/6 | 4/6 | 1 | 3 | 8 | 12 | 24 | 48 |
|---|---|---|---|---|---|---|---|---|---|---|---|---|---|
| 2 | Good | Fair | 84 | — | — | — | — | o | o | o | o | o | — |
| 3 | Good | Good | 64 | o | o | o | o | o | o | o | o | o | — |
| 4 | Good | Good | 68 | o | o | o | o | o | o | o | o | o | o |
| 5 | Good | Good | 85 | — | — | — | o | o | o | o | o | o | o |
| 6 | Good | Good | 73 | — | — | o | o | o | o | o | o | o | o |
| 7 | Good | Good | 72 | o | o | o | o | o | o | o | o | o | o |

Residual Content of Active Ingredient

A pharmaceutical preparation sample (5 cm×5 cm) was adhered to the inside of the human upper arm, and after 18 hours, was peeled off. The sample thus-peeled was dissolved in 30 ml of ethyl acetate at 40° C. for 26 hours while shaking. To the resulting solution was added ethyl acetate to make 50 ml. The thus-prepared solution was subjected to gas chromatographic quantitative determination. The residual content was determined with the initial amount of the active ingredient being taken as 100%.

Mobility of Active Ingredient to Skin

A pharmaceutical preparation sample (5 cm×5 cm) was sticked to the inside of the upper arm. The symbol "o" indicates that the skin turned red or a feeling of flushing was caused, and the symbol "—" indicates that such phenomena did not occur.

TABLE 2

| Example No. | Concentration of Active Ingredient in Blood after Application of Pharmaceutical Preparation (ng/ml) for Predetermined Time (hrs) | | | | | |
|---|---|---|---|---|---|---|
| | 0.5 | 1 | 3 | 8 | 24 | 48 |
| 1 | 0 | 0 | 2.1 | 3.1 | 1.3 | 0.5 |
| 2 | 0 | 0 | 3.8 | 7.1 | 4.1 | 0.7 |
| 3 | 6.3 | 9.8 | 11.0 | 6.3 | 4.9 | 3.8 |
| 4 | 7.3 | 10.1 | 10.9 | 5.4 | 5.8 | 2.4 |
| 5 | 0 | 0.9 | 3.1 | 4.1 | 3.9 | 4.9 |
| 6 | 0 | 1.1 | 6.7 | 7.3 | 6.1 | 3.1 |
| 7 | 4.1 | 4.8 | 5.7 | 6.0 | 5.3 | 5.1 |

Concentration of Active Ingredient in Blood

A pharmaceutical preparation sample (2 cm×4 cm) was adhered to the back of a rabbit (weight: 2 kg) on an area where the hair had been removed. After a predetermined period of time, 3 ml of blood was collected, and the plasma was separated therefrom. The thus-separated plasma was 2 ml of n-hexane for extraction. The mixture was subjected to centrifugal separation, and then the extract was concentrated to 0.5 ml under an atmosphere of inert gas. Then, the concentrate was extracted with 1 ml of acetonitrile. The acetonitrile layer thus-obtained was vaporized to dryness under inert gas, and the resulting residue was dissolved in 100 μl of benzene and was subjected to a gas chromatographic measurement.

The sample of Example 7 in Tables 1 and 2 had the same area as in Examples 1 to 6 but was designed so that the areas of the two base materials were equal.

As can be seen from the above examples, the pharmaceutical preparation of the invention exhibits excellent adhesion to the skin and good releasability of the active ingredient.

While the invention has been described in detail and with reference to specific embodiments thereof, it will be apparent to one skilled in the art that various changes and modifications can be made therein without departing from the spirit and scope thereof.

What is claimed is:

1. A pharmaceutical preparation comprising a flexible backing and a base material formed on the flexible backing, said base material comprising a layer of a polymer having a glass transition temperature (Tg) of from $-70°$ C. to $-10°$ C. and exhibiting pressure-sensitivity at room temperature, and isosorbide dinitrate (ISDN) or pentaerythritol tetranitrate (PETN) retained in said base material, wherein the polymer contains at least 50% by weight alkyl acrylate or methacrylate containing an average of at least 4 carbon atoms in the alkyl moiety, wherein the isosorbide dinitrate or pentaerythritol tetranitrate concentration in the base material is from 0.5 to 20% by weight and wherein the laminate is composed of a polyester and a member selected from an ethylene-vinylacetate copolymer and an ethylene-ethylacrylate copolymer which prevents the crystallization of the isosorbide dinitrate or pentaerythritol tetranitrate.

2. A pharmaceutical preparation as in claim 1, wherein the polymer is a copolymer of alkyl acrylate or methacrylate and a functional monomer copolymerizable therewith.

3. A pharmaceutical preparation as in claim 2, wherein the polymer is a copolymer of alkyl acrylate or methacrylate and a vinyl ester monomer copolymerizable therewith.

4. A pharmaceutical preparation as in claim 1, wherein the base material further contains an absorption promotor.

5. A pharmaceutical preparation as in claim 1, wherein the base material comprises a plurality of base materials, each of which is composed of a polymer having a different glass transition temperature.

6. A pharmaceutical preparation as in claim 1, 2, 3, 4, or 5, wherein the glass transition temperature (Tg) is from $-55°$ C. to $-25°$ C.

7. A pharmaceutical preparation as in claim 1, wherein the isosorbide dinitrate or pentaerythritol tetranitrate concentration in the base material is from 2 to 15% by weight.

8. A pharmaceutical preparation as in claim 1, 2, 3, 4, or 5, wherein the thickness of the base material is from 5 to 300 μm.

9. A pharmaceutical preparation as in claim 6, wherein the thickness of the base material is from 5 to 300 μm.

10. A pharmaceutical preparation as in claim 7, wherein the thickness of the base material is from 5 to 300 μm.

11. A pharmaceutical preparation as in claim 1, wherein the backing is a laminate.

* * * * *